United States Patent
Win et al.

(10) Patent No.: US 9,814,465 B2
(45) Date of Patent: Nov. 14, 2017

(54) MECHANICALLY DETACHABLE VASO-OCCLUSIVE DEVICE

(71) Applicant: Boston Scientific Scimed, Inc., Maple Grove, MN (US)

(72) Inventors: Thazin Win, Fremont, CA (US); Like Que, Livermore, CA (US); Esther Chang, Fremont, CA (US); Ann Huang, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 342 days.

(21) Appl. No.: 14/487,415

(22) Filed: Sep. 16, 2014

(65) Prior Publication Data
US 2015/0025566 A1    Jan. 22, 2015

Related U.S. Application Data

(63) Continuation of application No. 11/942,929, filed on Nov. 20, 2007, now Pat. No. 8,834,515.

(60) Provisional application No. 60/866,590, filed on Nov. 20, 2006.

(51) Int. Cl.
*A61B 17/12* (2006.01)
*A61B 17/00* (2006.01)

(52) U.S. Cl.
CPC .... *A61B 17/12109* (2013.01); *A61B 17/1214* (2013.01); *A61B 17/12022* (2013.01); *A61B 17/12113* (2013.01); *A61B 17/12145* (2013.01); *A61B 2017/0053* (2013.01); *A61B 2017/1205* (2013.01); *A61B 2017/12054* (2013.01); *A61B 2017/12095* (2013.01); *Y10T 29/49826* (2015.01)

(58) Field of Classification Search
CPC ...... A61F 2/01; A61F 2/013; A61F 2002/016; A61F 2002/011; A61B 17/12113; A61B 17/1214; A61B 17/12109
See application file for complete search history.

(56) References Cited

U.S. PATENT DOCUMENTS

| | | | | |
|---|---|---|---|---|
| 5,895,391 A | * | 4/1999 | Farnholtz | A61B 17/12022 606/108 |
| 5,925,059 A | * | 7/1999 | Palermo | A61B 17/12022 606/191 |
| 6,679,903 B2 | * | 1/2004 | Kurz | A61B 17/12022 606/200 |

(Continued)

*Primary Examiner* — Julie A Szpira (57) ABSTRACT

A device for delivering an occlusive element includes an elongate pusher member having a lumen. A locking member is disposed within the lumen of the elongate pusher member. A moveable elongate releasing member is disposed within the lumen of the elongate pusher member. A filament is secured to the distal end of the elongate releasing member. The occlusive member is locked to the elongate releasing member when the filament passes through a securing member on the occlusive member and is pinched or wedged between the looking member and the elongate releasing member. The occlusive element is in an unlocked state when the elongate releasing member is retracted proximally relative to the elongate pusher member. The filament, along with the elongate releasing member, are retracted proximally until the filament is detached or uncoupled from the securing member of the occlusive member.

20 Claims, 4 Drawing Sheets (56) References Cited

U.S. PATENT DOCUMENTS

| | | | | |
|---|---|---|---|---|
| 7,918,872 | B2* | 4/2011 | Mitelberg | A61B 17/12022 606/200 |
| 8,777,978 | B2* | 7/2014 | Strauss | A61B 17/12022 606/200 |
| 2005/0234505 | A1* | 10/2005 | Diaz | A61B 17/12022 606/200 |
| 2005/0283182 | A1* | 12/2005 | Pierce | A61B 17/12022 606/200 |
| 2006/0025801 | A1* | 2/2006 | Lulo | A61B 17/12022 606/200 |
| 2006/0025802 | A1* | 2/2006 | Sowers | A61B 17/12022 606/200 |
| 2006/0276826 | A1* | 12/2006 | Mitelberg | A61B 17/12022 606/200 |
| 2006/0276834 | A1* | 12/2006 | Balgobin | A61B 17/12022 606/200 |
| 2007/0021775 | A1* | 1/2007 | Vrba | A61M 25/09 606/200 |
| 2007/0055302 | A1* | 3/2007 | Henry | A61B 17/12022 606/200 |

* cited by examiner

MECHANICALLY DETACHABLE VASO-OCCLUSIVE DEVICE

CROSS REFERENCE TO RELATED APPLICATIONS

This application is a Continuation of co-pending U.S. patent application Ser. No. 11/942,929, filed Nov. 20, 2007, entitled "MECHANICALLY DETACHABLE VASO-OCCLUSIVE DEVICE", which claims priority to U.S. Patent Application Ser. No. 60/866,590, filed Nov. 20, 2006, entitled "MECHANICALLY DETACHABLE VASO-OSSLUSIVE DEVICE" and is incorporated by reference herein in its entirety.

FIELD OF THE INVENTION

The field of the invention generally relates to systems and delivery devices, for implanting vaso-occlusive devices for establishing an embolus or vascular occlusion in a vessel of a human or veterinary patient.

BACKGROUND OF THE INVENTION

Vaso-occlusive devices or implants are used for a wide variety of reasons, including treatment of infra-vascular aneurysms. A common vaso-occlusivee device takes the form of a soft, helically wound coil formed by winding a platinum (or platinum alloy) wire strand about s primary mandrel. The relative stiffness of the coil will depend, among other things, on its composition, the diameter of the wire strand, the diameter of the primary mandrel, and the pitch of the primary windings. The coil is then wrapped around a larger, secondary mandrel, and again heat treated to impart a secondary shape. For example, U.S. Pat. No. 4,094,069, issued to Ritchart et al., describes a vaso-occlusive coil that assumes a linear, helical primary shape when stretched for placement through the lumen of a delivery catheter, and a folded, convoluted secondary shape when released from the delivery catheter and deposited in the vasculature.

In order to deliver the vaso-occlusive coils to a desired site, e.g., an aneurysm, in the vasculature, it is well-known to first position a small profile, micro-catheter at the site using a steerable guidewire. Typically, the distal end of the micro-catheter is provided, either by the attending physician or by the manufacturer, with a selected pre-shaped bend, e.g., 45°, 90°, "J", "S", or other bending shape, depending on the particular anatomy of the patient, so that it will stay in a desired; position for releasing one or more vaso-occlusive coil(s) into the aneurysm once the guidewire is withdrawn. A delivery or "pusher" wire is then passed through the micro-catheter, until a vaso-occlusive coil coupled, to a distal end of the pusher wire is extended out of the distal end opening of the micro-catheter and into the aneurysm. The vaso-occlusive device is then released or "detached" from the end pusher wire, and the pusher wire is withdrawn back through the catheter. Depending on the particular needs of the patient, another occlusive device may then be pushed through the catheter and released at the same site.

One known way to release a vaso-occlusive coil from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of art ionic solution, such as blood or other bodily fluids. Thus, once the detachment zone exits out of the catheter distal end and is exposed in the vessel blood pool of the patient, a current applied to the conductive pusher wire completes a circuit with an electrode attached to the patient's skin, or with a conductive needle inserted through the skin at a remote site, and the detachment zone disintegrates due to electrolysis.

U.S. Pat. No. 5,122,136 issued to Guglielmi, et al. discloses a device in which a portion of the guidewire connected between the tip and the body of the guidewire is comprised of stainless steel and exposed to the bloodstream so that upon continued application of a positive current to the exposed portion, the exposed portion is corroded away at least at one location and the lip is separated from the body of the guidewire. The guidewire and a microcatheter are thereafter removed leaving the guidewire tip embedded in the thrombus formed within the vascular cavity.

One perceived disadvantage with vaso-occlusive devices that are deployed using electrolytic detachment is that the electrolytic process requires a certain amount of time to elapse to effectuate release of the vaso-occlusive element. This time lag is also a perceived disadvantage for vaso-occlusive delivery devices that utilize thermal detachment mechanisms, U.S. Pat. No. 8,966,392 issued to Gandhi, et al. discloses a vaso-occlusive device that uses a thermal detachment system.

Another detachment modality used to deploy vaso-occlusive elements uses mechanical detachment. U.S. Pat. No. 5,800,453 issued to Gia discloses embolic coils that have a receiving slot on one end. A catheter control wire or pusher guidewire having a hook which engages the coil's receiving slot is used as a coil pusher to eject the coil at the chosen site. The coils may also be placed within the lumen with a catheter in a nose-to-tail fashion and pushed into the body lumen. Pushing the coil assembly via the pusher from the distal end of the catheter body uncouples the distal most coil.

Another example of a mechanical detachment system is disclosed in U.S. Pat. No. 5,800,455 issued to Palermo et al. Palermo et al. discloses a delivery system that includes a coil having a clasp or hook located at one end. The clasp or hook includes a passageway for a control wire. The clasp interlocks with another clasp located on a distal end of a pusher member. The control wire is withdrawn in the proximal direction to release the coil.

Still other mechanical detachments systems have been proposed that use a fiber segment that is pulled in the proximal direction to decoupled the fiber from the embolic coil device. Examples of these systems may be found in U.S. Patent Application Publication Nos. 2008/0025803 A1 (coiled fiber), 2008/0025802 A1 (U-shaped fiber), and 2006/0025801 A1 (detachment filament).

One problem with certain existing mechanical detachment systems is that the junction between the embolic element and the releasing member moves during the detachment process which may adversely impact the placement of the embolic element within the aneurysm. Another complication is that mechanical detachment systems tend to have a stiff main section that complicates accurate placement of the delivery system at the desired location. Mechanical detachment systems also are perceived by physicians as being harder to use than other devices. In addition, certain mechanical detachment systems may jeopardize the integrity of the embolic element (e.g. coil) after detachment.

There thus is a need for a vaso-occlusive delivery system that utilizes mechanical detachment yet does not suffer from the aforementioned deficiencies. Such a system should be easy to use yet provide for consistent detachment of embolic elements in the desired location. Moreover, the delivery system should be able to release the embolic element without any recoil or other movement resulting from the detachment operation.

SUMMARY

In one embodiment, a device for delivering an occlusive element such as, for example, a vaso-occlusive coil, includes an elongate pusher member having a distal end and a proximal end and a lumen extending between the distal and proximal ends. A locking member is disposed within the lumen of the elongate pusher member. An elongate releasing member is disposed within the lumen of the elongate pusher member. The elongate releasing member has a proximal end and a distal end and is moveable within the lumen of the elongate pusher member (e.g. the elongate releasing member can be moved proximally and distally along the long axis of the elongate pusher member). A filament is secured to the distal end of the elongate releasing member. The occlusive member includes a securing member disposed at a proximal end thereof. The securing member of the occlusive member is locked to the elongate releasing member when the filament passes through the securing member and is pinched between the locking member and the elongate releasing member. The occlusive element is in an unlocked state when the elongate releasing member is retracted proximally relative to the elongate pusher member. The filament, along with the elongate releasing member, are retracted proximally until the filament is detached or uncoupled from the securing member of the occlusive member.

In one aspect of the invention, the looking member may include an edge or surface that pinches or wedges the filament against the elongate releasing member. In addition, the elongate releasing member may include a tapered distal end that engages with the edge or surface of the looking member.

A blocking member may be disposed on the distal end of the elongate pusher member. The blocking member includes an aperture or passageway dimensioned to permit passage of the filament but not the coil. The blocking member thus prevents the coil from being retracted into the elongate pusher member.

Optionally, the elongate pusher member may include a coil member disposed on a distal end thereof. The coil member imparts added flexibility to the distal region of the elongate pusher member.

In another aspect of the invention, a device of delivering an occlusive element such as, for instance, a vaso-occlusive coil includes an elongate pusher member having a distal end and a proximal end and a lumen extending between the distal and proximal ends. A coil member is secured to the distal end of the elongate pusher member to give the delivery device added flexibility at the distal end. An elongate releasing member is disposed within the lumen of the elongate pusher member and is moveable within the lumen. The elongate releasing member includes proximal and distal ends with a filament being secured to the distal end. The occlusive member includes a securing member disposed at a proximal end thereof. The securing member of the occlusive member is locked to the elongate releasing member when the filament passes through the securing member and is wedged between the locking member and the elongate releasing member. The occlusive element is in an unlocked state when the elongate releasing member is retracted proximally relative to the elongate pusher member.

In still another aspect of the invention, a method of making a vaso-occlusive coil includes the steps of loading a vaso-occlusive coil on a distal end of the elongate pusher member by passing a filament coupled to an elongate releasing member through a securing member of the vaso-occlusive coil. The vaso-occlusive coil is then locked to the elongate pusher member by advancing the elongate releasing member distally within the elongate pusher member so as wedge or pinch the filament between the elongate releasing member and a locking surface of the elongate pusher member. For deployment, the vaso-occlusive cell is then positioned adjacent to a deployment site such as, for instance, an aneurysm. The coil may be positioned by using a delivery catheter such as, for instance, a microcatheter. The coil is then released by retracting the elongate releasing member proximally relative to the elongate pusher member. Proximal retraction of the elongate releasing member eliminates the frictional pinching of the filament between the locking surface and the elongate releasing member. The filament can then be withdrawn proximally (in response to movement of the elongate releasing member) to de-couple from the securing member of the coil.

BRIEF DESCRIPTION OF THE DRAWINGS

FIG. 6 is a partial cross-sectional view the distal end of a delivery device. FIG. 6 illustrates proximal retraction of the elongate releasing member along with retraction of the filament. The filament is de-coupled from the coil.

DETAILED DESCRIPTION OF THE ILLUSTRATED EMBODIMENTS

Figure 1:
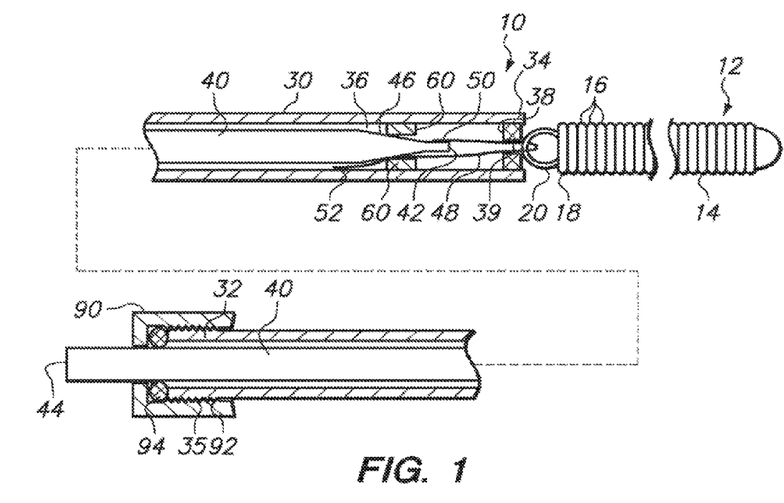
FIG. 1 is partial cross-sectional view of a delivery device according to one embodiment.
Figure 5:
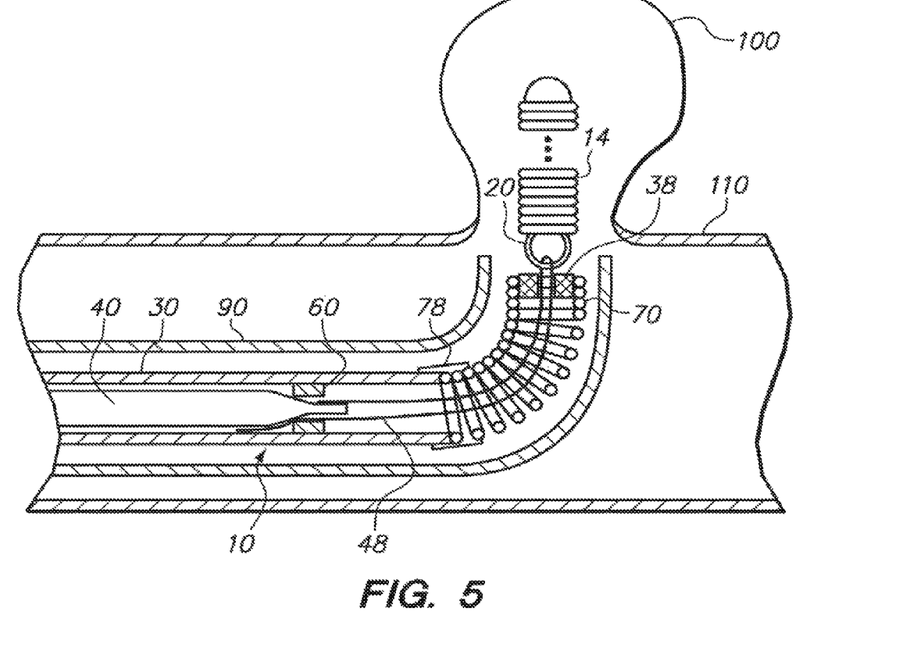
FIG. 5 is a cross-sectional view of a blood vessel having an aneurysm. A delivery device according to one embodiment is shown being deployed within a delivery catheter.

FIG. 1 illustrates a device 10 for delivering an occlusive element 12 to a vascular space such as, for example, aneurysm 100 (shown in FIG. 5). The occlusive element 12 may be formed as a vaso-occlusive coil 14 created from a plurality of coil windings 16. When manufacturing the vaso-occlusive coil 14, the coil material is wound into a coil shape, which will typically be linear. Generally speaking, the coil 14 is a metallic coil made from a platinum alloy or a super-elastic alloy such as titanium/nickel alloy, known as NITINOL. The diameter of the wire used in the production of the coils 14 may fall in the range of about 0.00025 inches to about 0.008 inches. The coil 14 may have a primary diameter of between about 0.003 and about 0.025 inches, but for most neurovascular applications, a diameter between about 0.008 to about 0.018 inches provides sufficient hoop strength to hold the coil 14 in place within the chosen body site, lumen, or cavity, without substantially distending the wall of the site and without moving from the site as a result of the repetitive fluid pulsing found in the vascular system.

The axial length of the coil wire will usually fall in the range of around 0.5 to around 100 cm, more usually around 2.0 to 40 cm. Of course, ail of the dimensions provided above should be viewed only as guidelines, and the invention, in its broader aspects, should not be limited thereto. Dimensions that are suitable for use in occluding sites within the human body are included in the scope of this invention.

Depending on the desired therapeutic elect and the shape of the site to be treated, the coil 14 may later be treated or accessorized in numerous ways in order to enhance its therapeutic effect. The coil 14 may be made to form various secondary shapes, often through the use of heat treatment, that may be better suited to fill a particular treatment site, as disclosed in U.S. Pat. Nos. 5,853,418 and 6,280,457, the entireties of which are expressly incorporated herein by reference. Alternatively, the coil 14 may have little or no shape after introduction into the vascular space, as disclosed in U.S. Pat. No. 5,690,886, the entirety of which is expressly incorporated by reference herein. In addition, external materials may be added to the outside of the coil 14 in an effort to increase its thrombolytic properties. These alternative embodiments are disclosed in U.S. Pat. Nos. 5,226,911, 5,304,194, 5,549,624, 5,382,259, and 6,280,457, the entireties of which are expressly incorporated herein by reference.

Still referring to FIG. 1, the proximal end 18 of the coil 14 includes a securing member 20. The securing member 20 may be formed as a closed loop, hoop, ring, or eyelet. Alternatively, the securing member 20 may be formed in an open configuration such as a book or the like (not shown). The loop, hoop, ring, or eyelet from of the securing member 20 has its two ends fixedly secured to a proximal end 18 of the coil 14. In one embodiment, the securing member 20 may be formed integrally with the coil 14. In this regard, the securing member 20 may be formed from a proximal winding of the coil 14. For example, the proximal winding may be looped back upon itself and optionally bonded to one or more windings 18 to form the closed securing member 20, Alternatively, the securing member 20 may be formed separately from the coil 14. For example, the securing member 20 may be formed from a thin metal wire filament such as platinum, NITINOL, titanium, stainless steel, and metallic alloys. Alternatively, the securing member 20 may be formed using a polymer-based material such as NYLON, PTFE, polypropylene, polyimide, PEEK, and the like. The separate securing member 20 may then be jointed to the proximal end 18 of the coil 14 either by tying or through bonding operation. For example, an adhesive material or a weld may be used to fixedly attach the securing member 20 to the proximal end 18 of the coil 14. If the securing member 20 is formed from a metallic material, the securing member 20 may be formed from a thin metal sheet using a photo-etching process. The liberated securing member 20 may then be jointed to the coil 14, for example, using a weld, solder, or adhesive.

Referring to FIG. 1, the delivery device 10 includes an elongate pusher member 30 having a proximal end 32 and a distal end 34. A lumen 36 is formed within the elongate pusher member 30. The elongate pusher member 30 may be formed as a sheath, hypotube or the like. Alternatively, the elongate pusher member 30 may be formed at least in part from a coiled structure created from a series of windings of material such as, for instance, metallic coil. In yet another alternative, at least a portion of the elongate pusher member 30 may be formed from a braided material to impart added flexibility. For example, a region near the distal end 34 of the elongate pusher member 30 may be formed from a coil or braid to ensure flexibility at the distal tip of the delivery device 10. In still another alternative, the distal end 34 of the elongate pusher member 30 may have a decreased stiffness as compared to the stiffness of the proximal end 32. For example, the distal end 34 of the elongate pusher member 30 may have a thinner wall thickness than the proximal end 32.

The elongate pusher member 30 may be formed from a flexible yet lubricious polymer material such as polyimide, polytetrafluoroethylene (PTFE), polyetheretherketone (PEEK), fluorinated ethylene propylene (FEP), polypropylene, or the like. The elongate pusher member 30 may also be formed using non-polymer materials. For example, one or more segments may be formed from metal hypotube formed from stainless steel, NITINOL, and the like. The elongate pusher member 30 generally has a length that permits the same to be advanced intravascularly to the site of interest. For example, the elongate pusher member 30 has a length to permit the distal end 34 to be positioned adjacent to the delivery site (e.g., aneurysm 100) while the proximal end 32 is positioned outside the patient's body. A typical range of lengths for the elongate sheath 30 may include between about 1.25 to about 2.0 meters.

As seen in FIG. 1, a blocking member 38 is disposed at the distal end 34 of the elongate pusher member 30. The blocking member 38 includes an aperture 39 sized to permit passage of a filament 48 (described in more detail below). The size of the aperture 39 is dimensioned such that the filament 48 can pass through but not the coil 14. In some cases, the aperture 39 may be dimensioned to permit passage of at least a portion of the securing member 20. However, the aperture 39 still prevents the coil 14 from retracting inside the elongate pusher member 30. The blocking member 38 may be formed from a short segment of tubing such as, for instance, stainless steel hypotube, or a polymer-based tube (e.g., polyimide, PEEK, or the like). Alternatively, the blocking member 38 may be formed from a short segment of coil (not shown) that resides inside the lumen 36 of the elongate pusher member 30. The blocking member 38 may be bonded or jointed to the elongate pusher member 30 using an adhesive, solder, or weld. In addition, it is also contemplated that the blocking member 38 may abut against the distal end 34 of the elongate pusher member 30.

The device 10 includes an elongate releasing member 40 disposed within the lumen 36 of the elongate sheath 30. The elongate releasing member 40 has a distal end 42 and a proximal end 44. The elongate releasing member 40 is formed from a flexible yet sturdy material that provides sufficient columnar strength to avoid breakage during the deployment process. For example, the elongate releasing member 40 may be formed from a wire made from a metal or alloy such as NITINOL, titanium, stainless steel or the like.

As seen in FIGS. 1-7, the elongate releasing member 40 includes a tapered section 46 located at the distal end 42. The tapered section 46 may be formed by grinding a wife or the like. As described in more detail below, the tapered section 46, pushes the filament 48 against a locking member 60 and is used as an engaging surface to temporarily look the elongate releasing member 40 relative to the elongate pusher member 30. The filament 48 is pinched between the tapered section 46 and locking member 60 and is prevented from moving distally so as to keep the coil 14 from being released prematurely.

Still referring to FIG. 1, a locking member 60 is provided inside the lumen 36 of the elongate pusher member 30. The locking member 60 is located near the distal end 34 of the elongate pusher member 30 and may be formed as a tube or coil. For example, the locking member 60 may be formed from a short segment of stainless steel or NITINOL hypotube. Alternatively, the locking member 60 may be created from a short segment of stainless steel or platinum coil. The locking member 60 may be bonded or jointed to the interior of the elongate pusher member 30 using a weld, solder, adhesive, or the like. The locking member 60 includes an locking surface 60a (FIG. 3) that contacts the tapered section 46 of the elongate releasing member 40 during the locking operation.

In still another aspect of the invention, the locking surface 60a may be integrated directly into the elongate pusher member 38. For example, the locking member 60 may be formed as part of the elongate pusher member 30.

As seen in FIG. 1, a filament 48 is disposed on the distal end 42 of the elongate releasing member 40 and includes a proximal end 50 and a distal end 52. The filament 48 is used to releaseably secure the coil 14 to the elongate releasing member 40. The filament 48 may be formed as a string, wire, or cable. For example, the filament 48 may be formed from a metallic material such as, for instance, NITINOL, stainless steel, or titanium. Alternatively, the filament 48 may be formed from a polymer material such as polyethylene terephthalate (PET), fluorinated ethylene propylene (FEP), polypropylene, polyethylene napthalate (PEN), or the like. Of course, other materials beyond those expressly listed above may also be used. The filament 48 may constructed of a single strand or may comprise multiple strands in a braided or wound configuration.

The length of the filament 48 may vary. For example, the filament 48 may be formed from a relatively short segment such as in the embodiments illustrated in FIGS. 1-6. Alternatively, the length of the filament 48 may be relatively long such as disclosed in the embodiment shown in FIG. 7. The filament 48 should have a length that permits the same to pass through the securing member 20 and backtrack proximally with respect to the locking member 60 to permit locking. The proximal end 50 of the filament 48 may be secured to the distal end 42 of the elongate releasing member 40 by a weld, adhesive, or the like. Alternatively, the elongate releasing member 40 and filament 48 can be integrated into or formed having a unitary construction. For example, a single wire may be used that has a relatively thick proximal section 40, a tapered section 46, and a thin filament 48.

The elongate releasing member 40 is moveable (e.g., slidable) within the lumen 36 of the elongate pusher member 30. The elongate releasing member 40 is moveable between a locked configuration and an unlocked configuration. FIGS. 1-5 and 7 illustrates the elongate releasing member 40 being advanced distally to "lock" the coil 14 to the elongate pusher member 30. Referring to FIG. 1, the filament 48 that is secured to the distal end 42 of the elongate releasing member 40 passes through the securing member 20 located on the coil 14 and returns along side a portion of the elongate releasing member 40. The filament 48 is thus wedged or pinched between the locking member 60 and the tapered section 46 of the elongate releasing member 40. FIG. 3 illustrates a magnified view of the filament 48 being pinched or wedged between the locking member 60 and the elongate releasing member 40.

Figure 3:
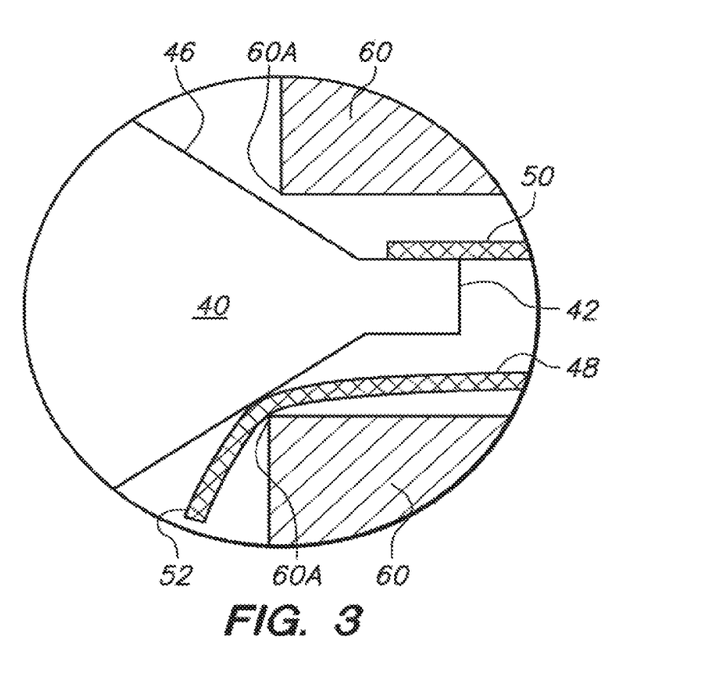
FIG. 3 is an enlarged cross-sectional view of the distal end of an elongate releasing member engaging with a locking member so as to fixedly secure a filament attached to the elongate releasing member.
Figure 4:
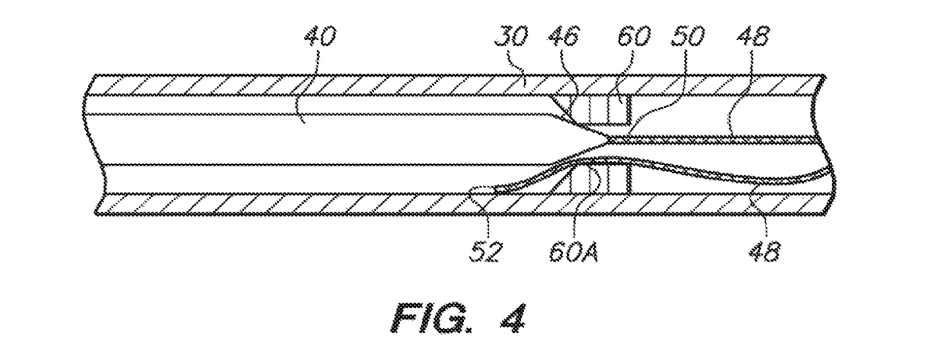
FIG. 4 is a cross-sectional view of a distal portion of a delivery device according to another aspect of the invention.

In the locked configuration, the coil 14 is securely fastened to the filament 48, Frictional engagement of the filament 48 between the locking member 60 and the elongate releasing member 40 thus prevent the filament 48 from retracting through the securing member 20 of the coil 14. While FIGS. 1-3 and 5-7 illustrate the locking member 60 having a locking surface 60a in the shape of an edge (shown best in FIG. 3) that forms as a pinch point, it should be understood that a surface may also be used as the pinch point. For example, FIG. 4 illustrate one embodiment of a locking member 60 in which an angled surface is used as the locking surface 60a to secure the filament 48.

Figure 8:
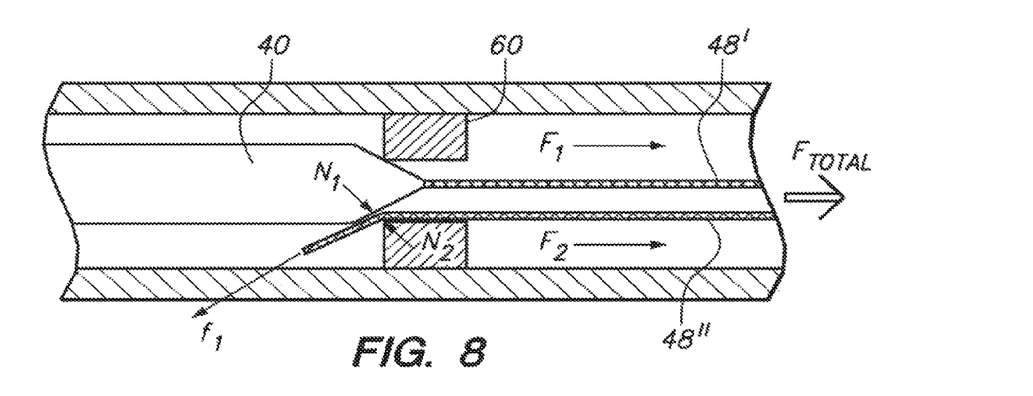
FIG. 8 illustrates a force diagram of a cross-sectional view of a distal region of a delivery device.

In one embodiment, a tight or friction fit is formed between the elongate releasing member 40 and the locking member 60, thereby requiring a certain threshold amount of retracting force (in the proximal direction) before the elongate releasing member 40 can move relative to the elongate pusher member 30. To illustrate a self-locking mechanism of the type described herein, FIG. 8 illustrates a force diagram that shows the various forces imparted to the filament 48. When the occlusion coil 14 is pulled away (distally) from the elongate pusher member 30 by a force F, it transforms into forces $F_1$ and $F_2$ on the two segments of filament 48' and 48" passing through securing member 20. $F_1$ will then pull the tapered section 46 toward the locking member 60 and generate compressive tomes $N_1$ and the resultant reaction force $N_2$. $N_1$ will then generate friction force $f_1$, wherein $f_1$=friction coefficient×$N_1$. When $f_1$ is greater than or equal to $F_2$, the filament member 48" will not be pulled away from its position, thus ensuring a locked configuration of the coil 14.

Figure 2:
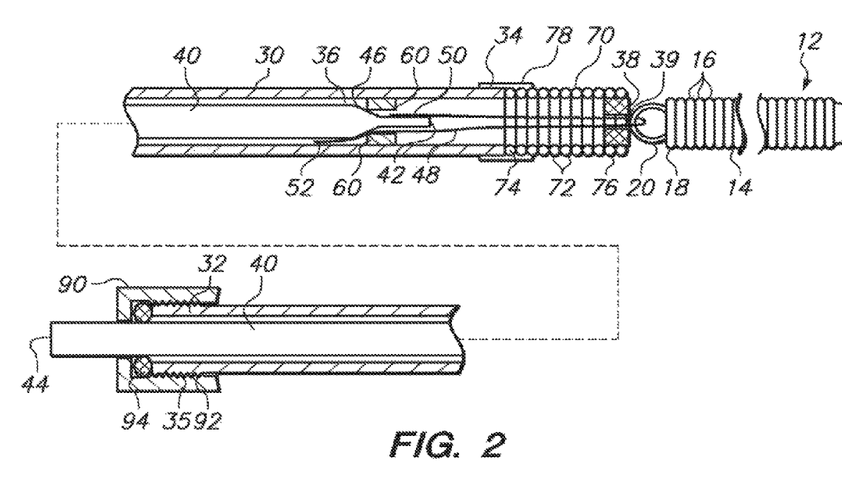
FIG. 2 is a partial cross-sectional view of a delivery device according to another embodiment.
Figure 7:
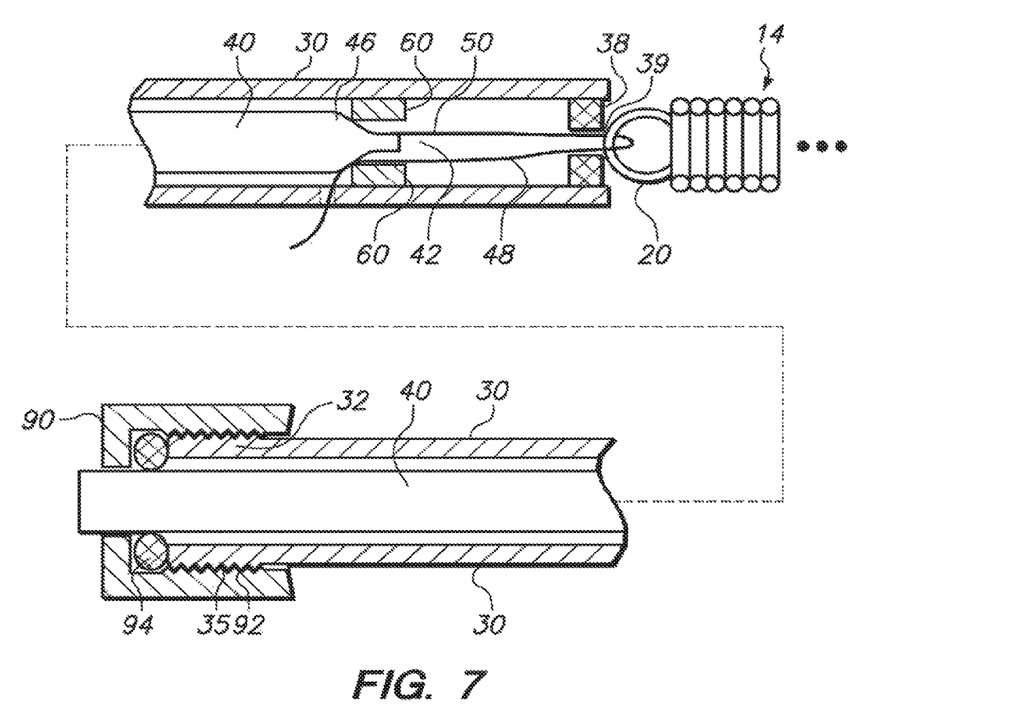
FIG. 7 illustrates a cross-sectional view of a delivery device according to one embodiment. The filament coupled to the elongate releasing member is shown passing through a lumen or passageway in the elongate pusher member.

As seen in FIGS. 1, 2, and 7, the proximal end 32 of the elongate pusher member 30 includes a locking member 90. The locking member 90 is used to fixedly secure the elongate releasing member 40 relative to the elongate pusher member 30. This may be accomplished by the use of a cap or the like such as that illustrated in FIG. 1 that is bonded or otherwise engaged with the elongate releasing member 40. For example, the elongate pusher member 30 may have a series of threads 35 on the exterior surface that engage with corresponding grooves 92 in the locking member 90. In the configuration shown in FIG. 1, the locking member 90 includes a compressible O-ring 94. When the locking member 90 is screwed onto the proximal end 32 of the elongate pusher member 30, the O-ring 94 undergoes radial expansion and grips the elongate releasing member 40. In this regard, the elongate releasing member 40 cannot be moved in either the proximal or distal directions. In order to deploy the coil 14, the locking member 90 must first be released from the elongate pusher member 30 by unscrewing the same from the threads 35.

FIG. 2 illustrates an alternative embodiment of a delivery device 10. This embodiment is similar to the embodiment illustrated in FIG. 1 with the exception that a coil member 70 is secured to the distal end 34 of the elongate pusher member 30. The coil member 70 may be formed from a plurality of windings 72 of wire (e.g., metallic or alloy such as platinum, stainless steel, titanium, and the like). The coil member 70 may be flexed about the its long axis such that the delivery device 10 incorporating this feature has added flexibility to reduce microcatheter recoil or kick-back. The coil member 70 may be coated or otherwise encapsulated in a sheath (not shown in FIG. 2), The coil member 70 may inserted into the lumen 38 of the elongate pusher member 30

(not shown). In this regard, a proximal end 74 of the coil member 70 may be bonded to an interior surface of the elongate pusher member 30. The coil member 70 may be bonded using a weld, solder, adhesive, or other known technique. Alternatively, as is shown in FIG. 2, the coil member 70 may abut against the distal most end 74 of the elongate pusher member 30. A surrounding jacket or sheath 78 may be used to secure the coil member 70 to the elongate pusher member 30. Still referring to FIG. 2, the blocking member 38 is disposed in a distal end 76 of the coil member 70. The blocking member 38 may be bonded to the coil member 70 via a weld, solder, or the use of an adhesive or other bonding agent.

FIG. 5 illustrates a process of delivering the coil 14 to an aneurysm 100 in a blood vessel 110. As seen in FIG. 5, a catheter device 90 such as a microcatheter is positioned within the vessel 110 so as to place the distal tip adjacent to the entry point or neck of the aneurysm 100. The device 10 of the type described herein is then advanced through the catheter 90. The device 10 is advanced to place the coil 14 located at the distal end of the elongate pusher member 30 at least partially within the aneurysm 100. One or more radiopaque markers (not shown) located on the catheter 90 and/or elongate pusher member 30, or on the elongate releasing member 40, may be used to aid the physician in positioning the device 10 for deployment of the coil 14.

The coil 14 may be loaded onto the delivery device 10 by passing the distal end 52 of the filament 43 through the securing member 20 of the coil 14. The elongate releasing member 40 may need to be partially advanced within the lumen 36 of the elongate pusher member 30 to ensure there is enough length of available filament 48. The distal end 52 of the filament 48 is pulled back proximally through the blocking member 38 and the locking member 60. When the distal end 52 of the filament 48 is proximal to the locking member 60, the elongate releasing member 40 is advanced distally so as to pinch the filament 48 between the tapered section 46 and the locking member 60. In the locked state, the elongate releasing member 40 is in a compressive state so as to fixedly secure or pinch the filament 48 against the locking member 60. The coil 14 is now locked relative to the elongate pusher member 30.

FIG. 7 illustrates one alternative embodiment in which the filament 48 is fed through passageway 82 in the elongate pusher member 30. The filament 48 then exits the passageway 82. In this embodiment, the filament 48 can be pulled taut during the loading of the coil 14. In particular, the filament 48 may be pulled proximally while the elongate releasing member 40 is advanced distally to lock the filament 48 into place. Any extra length in the filament 48 which protrudes from the elongate pusher member 30 can be clipped or trimmed off as appropriate.

In one embodiment, a locking member 90 located on the proximal end 32 of the elongate pusher member 30 may temporarily secure the elongate releasing member 40. Namely, the cap may prevent the elongate releasing member 40 from accidentally being withdrawn in the proximal direction, thereby causing premature release of the coil 14. The mechanical lock (e.g., cap) may be twisted, unscrewed or otherwise removed or unloosened to permit movement between the elongate pusher member 30 and the elongate releasing member 40. In another alternative, an adhesive, epoxy or glue may be used to temporarily lock the elongate releasing member 40 relative to the elongate pusher member 30. The temporary locking state between the elongate releasing member 40 and the elongate pusher member 30 may be opened by pulling the elongate releasing member 40 proximally relative to the elongate pusher member 30. For example, the adhesive bond may be broken once a certain level of retracting force is applied to the elongate releasing member 40.

Figure 6:
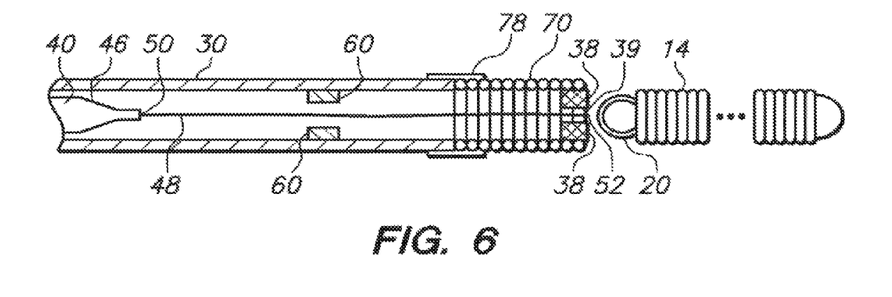

FIG. 6 illustrates the deployment of the coil 14 from the delivery device 10. Deployment is initiated by retracting the elongate releasing member 40 in the proximal direction relative to the elongate pusher member 30. For example, a physician may hold the elongate pusher member 30 with one hand while using the other hand to pull or retract the elongate releasing member 40. When the elongate releasing member 40 is retracted proximally, the filament 48 is no longer wedged or pinched between the tapered section 48 and the locking member 60. In this regard, the filament 48 can be withdrawn through the securing member 20 of the coil 14. The coil 14 is fully released when the filament 48 completely retracts from the securing member 20 as is illustrated in FIG. 6.

Once the coil 14 is released from the delivery device 10, the elongate pusher member 30 may then be retrieved from the body by withdrawing the elongate pusher member 30 together with the elongate releasing member 40 and attached filament 48 in the proximal direction. If additional coils 14 need to be deployed, then another delivery device 10 with a coupled coil 14 may be advanced through the catheter 90 as described above. After ail the coil(s) 14 have been deployed, the catheter 90 is then withdrawn from the vessel 110.

One advantage of the delivery device 10 described herein is that a pull-to-release process is used to deploy the coil 14. Because a pulling motion is used, there is no risk of poking or puncturing the aneurysm 100 that is inherent in push-based delivery devices. In this regard, the detachment of the coil 14 from the filament 48 is atraumatic. In addition, because the coupling between the coil 14 and the elongate releasing member 40 is mechanical, detachment is faster than electrolytic-based delivery devices. Finally, the nature of coupling between the coil 14 and the elongate releasing member 40 produces a smooth release of the coil 14 during deployment. For example, the delivery device 10 has reduced kick-back or recoil.

While embodiments of the present invention have been shown and described, various modifications may be made without departing from the scope of the present invention. The invention, therefore, should not be limited, except to the following claims, and their equivalents.

What is claimed is:

1. A method of loading a vaso-occlusive coil on a distal end of an elongate pusher member, comprising:
    passing a filament coupled to an elongate releasing member through a securing member of the vaso-occlusive coil to form a loop; and
    locking the vaso-occlusive coil to the elongate pusher member by advancing the elongate releasing member distally within the elongate pusher member so as to wedge a distal end of the filament loop between the elongate releasing member and a locking surface disposed in a lumen of the elongate pusher member.

2. The method of claim 1, wherein the locking surface of the elongate pusher member comprises a locking member disposed within a lumen of the elongate pusher member.

3. The method of claim 1, wherein the elongate pusher member includes a flexible distal end.

4. The method of claim 1, wherein a blocking member is disposed at a distal end of the elongate pusher member, the blocking member including an aperture dimensioned to receive the filament but prevent passage of the securing member.

5. The method of claim 1, wherein during the step of loading the vaso-occlusive coil, the filament is retracted proximally.

6. The method of claim 2, wherein the locking member includes one of an edge and a surface that pinches the filament against the elongate releasing member.

7. The method of claim 2, wherein the elongate releasing member includes a tapered portion, wherein the filament is wedged between the tapered portion and the locking member in a locked configuration.

8. The method of claim 1, wherein the distal end of the elongate pusher member includes a stiffness that is less than a stiffness of a proximal end of the elongate pusher member.

9. The method of claim 1, wherein the distal end of the elongate pusher member comprises a coil member.

10. The method of claim 1, wherein the securing member is formed from a proximal winding of the vaso-occlusive coil.

11. A method of deploying a vaso-occlusive coil from a distal end of an elongate pusher member, comprising:
    positioning the vaso-occlusive coil adjacent to a deployment site, wherein the vaso-occlusive coil is attached to the distal end of the elongate pusher member by a filament loop coupled to an elongate releasing member;
    wherein the elongate releasing member includes a tapered portion, wherein the filament is wedged between the tapered portion and the elongate pusher member in a locked configuration; and
    retracting the elongate releasing member proximally relative to the elongate pusher member so as to release the vaso-occlusive coil from the filament loop.

12. The method of claim 11, further comprising the step of removing the elongate pusher member from a patient.

13. The method of claim 11, further comprising locking the elongate releasing member relative to the elongate pusher member after loading the vaso-occlusive coil.

14. The method of claim 13, further comprising unlocking the elongate releasing member relative to the elongate pusher member prior to release of the vaso-occlusive coil.

15. The method of claim 11, wherein the distal end of the elongate pusher member comprises a coil member.

16. The method of claim 11, wherein a proximal winding of the vaso-occlusive coil forms a securing member configured to receive the filament loop.

17. A method of deploying a vaso-occlusive coil from a distal end of an elongate pusher member, comprising:
    positioning the vaso-occlusive coil adjacent to a deployment site, wherein the vaso-occlusive coil is attached to the distal end of the elongate pusher member by a filament loop coupled to an elongate releasing member;
    wherein the distal end of the elongate pusher member includes a stiffness that is less than a stiffness of a proximal end of the elongate pusher member; and
    retracting the elongate releasing member proximally relative to the elongate pusher member so as to release the vaso-occlusive coil from the filament loop.

18. The method of claim 17, further comprising locking the elongate releasing member relative to the elongate pusher member after loading the vaso-occlusive coil.

19. The method of claim 17, wherein the distal end of the elongate pusher member comprises a coil member.

20. The method of claim 17, wherein a proximal winding of the vaso-occlusive coil forms a securing member configured to receive the filament loop.

\* \* \* \* \*